(12) United States Patent
Harrison

(10) Patent No.: US 6,360,746 B1
(45) Date of Patent: Mar. 26, 2002

(54) ORAL PROPHYLACTIC DEVICE

(76) Inventor: Terrance Harrison, 15433 Elm La., Chino Hills, CA (US) 91709

( * ) Notice: Subject to any disclaimer, the term of this patent is extended or adjusted under 35 U.S.C. 154(b) by 0 days.

(21) Appl. No.: 09/805,008

(22) Filed: Mar. 12, 2001

(51) Int. Cl.[7] .................................................. A61F 6/02
(52) U.S. Cl. ........................ 128/842; 128/844; 128/918; 128/859
(58) Field of Search ................................ 128/842, 844, 128/848, 859, 918; 433/6, 93, 137

(56) References Cited

U.S. PATENT DOCUMENTS

| | | | | |
|---|---|---|---|---|
| 4,721,465 A | * | 1/1988 | Barmex | 433/137 |
| 4,949,731 A | * | 8/1990 | Harding | 128/842 |
| 5,449,486 A | * | 9/1995 | Hopkins | 128/918 |
| 5,582,187 A | * | 12/1996 | Hussey | 128/842 |
| 6,213,772 B1 | * | 4/2001 | Castello | 433/93 |

* cited by examiner

Primary Examiner—Michael A. Brown
(74) Attorney, Agent, or Firm—Goldstein Law Offices, PC

(57) ABSTRACT

An oral prophylactic device including a peripheral frame constructed of a thick and pliable latex material. The peripheral frame forms a central opening. The peripheral frame includes an upper segment, a lower segment, and opposed side segments in a generally square configuration. The lower segment has an arcuate central portion. The peripheral frame includes four corners each having a flex slot formed therein. A thin layer of latex is disposed loosely within the central opening of the peripheral frame.

1 Claim, 1 Drawing Sheet

ORAL PROPHYLACTIC DEVICE

BACKGROUND OF THE INVENTION

The present invention relates to an oral prophylactic device and more particularly pertains to protecting a person from being transmitted a disease while performing oral sex on a woman.

The use of prophylactic devices is known in the prior art. More specifically, prophylactic devices heretofore devised and utilized for the purpose of preventing the transmission of disease are known to consist basically of familiar, expected and obvious structural configurations, notwithstanding the myriad of designs encompassed by the crowded prior art that have been developed for the fulfillment of countless objectives and requirements.

By way of example, U.S. Pat. No. 4,949,731 to Harding discloses an oral prophylactic device comprising elastic flexible material to conform to the mouth for oral use. U.S. Pat. No. 5,409,016 to Bloodsaw and U.S. Pat. No. 5,649,549 to Saba disclose additional contraceptive devices for oral sex to prevent the spread of disease.

While these devices fulfill their respective, particular objective and requirements, the aforementioned patents do not describe an oral prophylactic device for protecting a person from being transmitted a disease while performing oral sex on a woman.

In this respect, the oral prophylactic device according to the present invention substantially departs from the conventional concepts and designs of the prior art, and in doing so provides an apparatus primarily developed for the purpose of protecting a person from being transmitted a disease while performing oral sex on a woman.

Therefore, it can be appreciated that there exists a continuing need for a new and improved oral prophylactic device that can be used for protecting a person from being transmitted a disease while performing oral sex on a woman. In this regard, the present invention substantially fulfills this need.

SUMMARY OF THE INVENTION

In the view of the foregoing disadvantages inherent in the known types of prophylactic devices now present in the prior art, the present invention provides an improved oral prophylactic device. As such, the general purpose of the present invention, which will be described subsequently in greater detail, is to provide a new and improved oral prophylactic device that has all the advantages of the prior art and none of the disadvantages.

To attain this, the present invention essentially comprises a peripheral frame constructed of a thick and pliable latex material. The peripheral frame forms a central opening. The peripheral frame includes an upper segment, a lower segment, and opposed side segments in a generally square configuration. The lower segment has an arcuate central portion. The peripheral frame includes four corners each having a flex slot formed therein. A thin layer of latex is disposed loosely within the central opening of the peripheral frame.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved oral prophylactic device that has all the advantages of the prior art prophylactic devices and none of the disadvantages.

It is another object of the present invention to provide a new and improved oral prophylactic device that may be easily and efficiently manufactured and marketed.

It is a further object of the present invention to provide a new and improved oral prophylactic device that is of durable and reliable construction.

An even further object of the present invention is to provide a new and improved oral prophylactic device that is susceptible of a low cost of manufacture with regard to both materials and labor, and which accordingly is then susceptible of low prices of sale to the consuming public, thereby making such an oral prophylactic device economically available to the buying public.

Even still another object of the present invention is to provide a new and improved oral prophylactic device for protecting a person from being transmitted a disease while performing oral sex on a woman.

Lastly, it is an object of the present invention to provide a new and improved oral prophylactic device including a peripheral frame constructed of a thick and pliable latex material. The peripheral frame forms a central opening. The peripheral frame includes an upper segment, a lower segment, and opposed side segments in a generally square configuration. The lower segment has an arcuate central portion. The peripheral frame includes four corners each having a flex slot formed therein. A thin layer of latex is disposed loosely within the central opening of the peripheral frame.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
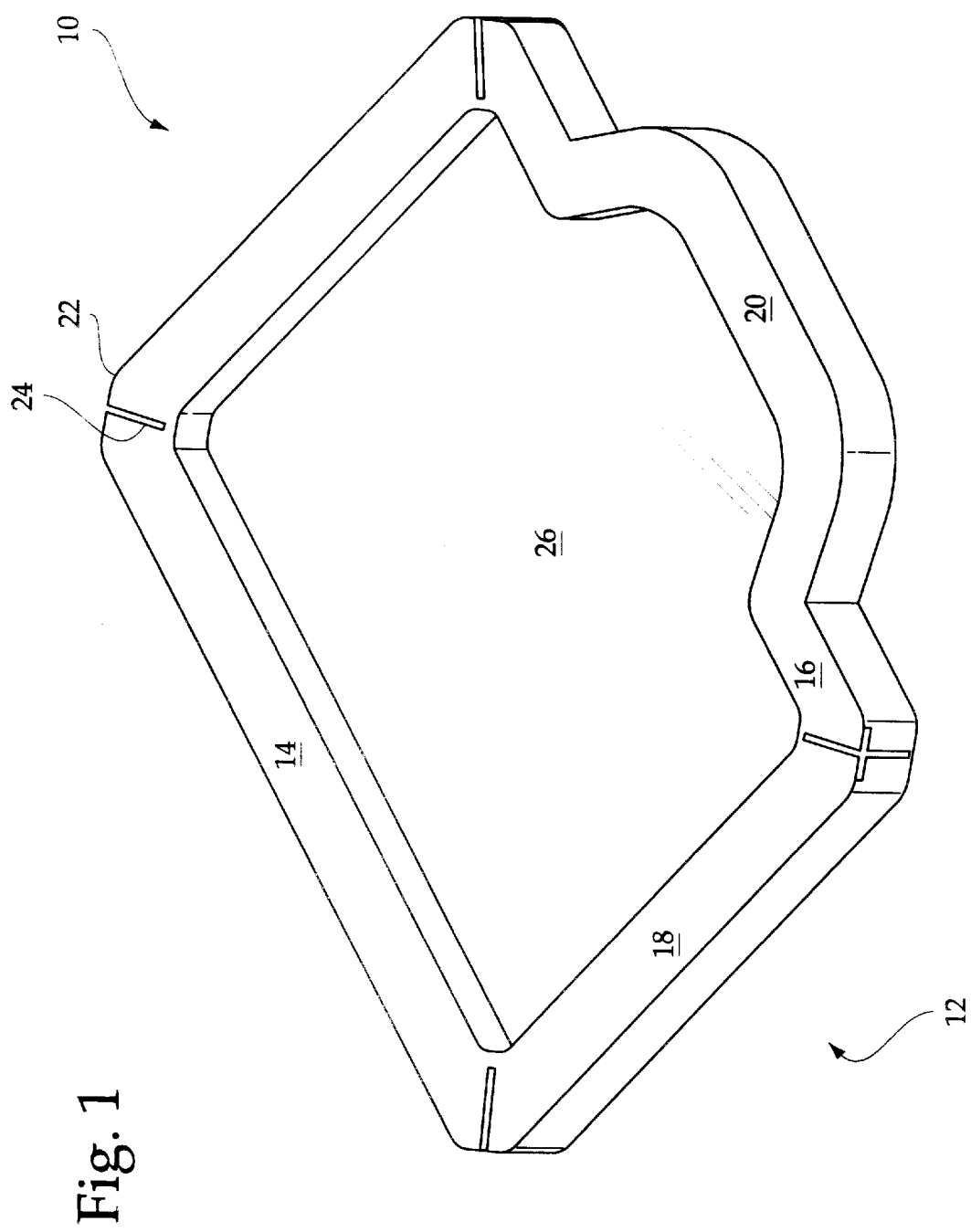
FIG. 1 is a perspective view of the preferred embodiment of the oral prophylactic device constructed in accordance with the principles of the present invention.

With reference now to the drawings, and in particular, to FIG. 1 thereof, the preferred embodiment of the new and improved oral prophylactic device embodying the principles and concepts of the present invention and generally designated by the reference number 10 will be described.

Specifically, it will be noted in the various figures that the device relates to an oral prophylactic device for protecting a person from being transmitted a disease while performing oral sex on a woman. In its broadest context, the device consists of a peripheral frame and a thin layer of latex. Such components are individually configured and correlated with respect to each other so as to attain the desired objective.

The peripheral frame 12 is constructed of a thick and pliable latex material. This allows the peripheral frame 12 to be properly positioned between the legs of a woman. The peripheral frame 12 forms a central opening. The peripheral frame 12 includes an upper segment 14, a lower segment 16, and opposed side segments 18 in a generally square configuration. The lower segment 16 has an arcuate central portion 20. The arcuate central portion 20 is provided with a greater degree of flexibility than the rest of the peripheral frame 12. The peripheral frame 12 includes four corners 22 each having a flex slot 24 formed therein. The flex slot 24 facilitates the overall flexibility of the peripheral frame 12.

The thin layer of latex 26 is disposed loosely within the central opening of the peripheral frame 12. The thin layer of latex 26 will be positioned over the private parts of the woman. Additionally, the thin layer of latex 26 can optionally be removed from the peripheral frame 12 and replaced prior to a next usage.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An oral prophylactic device for protecting a person from being transmitted a disease while performing oral sex on a woman comprising, in combination:

a peripheral frame constructed of a thick and pliable latex material, the peripheral frame forming a central opening, the peripheral frame including an upper segment, a lower segment, and opposed side segments in a generally square configuration, the lower segment having an arcuate central portion, the peripheral frame including four corners each having a flex slot formed therein; and a thin layer of latex disposed loosely within the central opening of the peripheral frame.

* * * * *